(12) United States Patent
Jang et al.

(10) Patent No.: US 10,684,180 B2
(45) Date of Patent: *Jun. 16, 2020

(54) METHOD AND DEVICE FOR SENSING PAIN

(71) Applicant: Daegu Gyeongbuk Institute of Science and Technology, Dalseong-gun, Daegu (KR)

(72) Inventors: Jae Eun Jang, Daegu (KR); Kyung Hwa Lee, Daegu (KR); Minkyung Sim, Gyeongsangnam-do (KR); Cheil Moon, Daegu (KR); Ji-Woong Choi, Daegu (KR); Hongsoo Choi, Daegu (KR)

(73) Assignee: Daegu Gyeongbuk Institute of Science and Technology, Dalseong-gun, Daegu (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/983,878

(22) Filed: May 18, 2018

(65) Prior Publication Data
US 2018/0266899 A1    Sep. 20, 2018

Related U.S. Application Data

(63) Continuation of application No. 15/235,395, filed on Aug. 12, 2016, now Pat. No. 10,001,422.

(30) Foreign Application Priority Data

Aug. 13, 2015 (KR) .................. 10-2015-0114711

(51) Int. Cl.
*G01L 1/16* (2006.01)
*A61B 5/00* (2006.01)
*G06N 3/00* (2006.01)

(52) U.S. Cl.
CPC .............. *G01L 1/16* (2013.01); *A61B 5/4824* (2013.01); *G06N 3/008* (2013.01); *A61B 2562/0247* (2013.01); *A61B 2562/046* (2013.01)

(58) Field of Classification Search
CPC .. G01L 1/00; G01L 1/205; G01L 1/16; G01N 2291/106; G06N 3/008; A61B 5/4824; A61B 2562/0247; A61B 2562/046
(Continued)

(56) References Cited

U.S. PATENT DOCUMENTS 6,459,804 B2    10/2002  Mainguet
6,826,426 B2 *  11/2004  Lange ................. A61B 5/0478
                                                  600/300
(Continued)

FOREIGN PATENT DOCUMENTS

JP    06281516       10/1994
JP    2006105964 A    4/2006
(Continued)

OTHER PUBLICATIONS

Korean-language Notice of Allowance issued in counterpart Application No. KR 10-2015-0114711 dated Dec. 29, 2017 (six (6) pages).
(Continued)

*Primary Examiner* — Octavia Hollington
(74) *Attorney, Agent, or Firm* — Nathan P. Letts; Olive Law Groups, PLLC

(57) ABSTRACT

A pain sensing device includes a sensor array including a plurality of sensors that sense pressure generated due to a contact of an object and output electrical piezoelectric signals; and a signal processor configured to recognize the shape of the object based on the number of sensors that output the piezoelectric signals among the plurality of
(Continued)

sensors, and to generate a pain signal according to the recognized shape of the object.

7 Claims, 13 Drawing Sheets

(58) Field of Classification Search
USPC .................................. 73/862.041–862.046
See application file for complete search history.

(56) References Cited

U.S. PATENT DOCUMENTS

| | | | |
|---|---|---|---|
| 7,331,245 B2* | 2/2008 | Nishimura | G06F 3/0414 73/818 |
| 8,583,239 B2* | 11/2013 | Pless | A61N 1/36071 607/46 |
| 8,749,120 B2 | 6/2014 | Liu et al. | |
| 8,764,650 B2 | 7/2014 | Schiavenato et al. | |
| 8,858,433 B2 | 10/2014 | Sethi et al. | |
| 9,035,776 B2* | 5/2015 | Miller, II | A42B 3/046 340/573.1 |
| 2003/0204148 A1 | 10/2003 | Lange et al. | |
| 2007/0135689 A1 | 6/2007 | Asukai et al. | |
| 2007/0176515 A1 | 8/2007 | Nagaya et al. | |
| 2012/0130196 A1* | 5/2012 | Jain | A61B 5/0022 600/300 |
| 2013/0081450 A1 | 4/2013 | Son et al. | |
| 2013/0106244 A1 | 5/2013 | Liu et al. | |
| 2014/0039351 A1* | 2/2014 | Mix | A61B 5/1114 600/587 |
| 2017/0136264 A1 | 5/2017 | Hyde et al. | |
| 2019/0021650 A1* | 1/2019 | Lee | A61B 5/7242 |

FOREIGN PATENT DOCUMENTS

| | | |
|---|---|---|
| JP | 3953024 B2 | 8/2007 |
| JP | 2007333522 A | 12/2007 |
| JP | 4408965 B2 | 2/2010 |
| KR | 1020080032316 A | 4/2008 |
| KR | 100995895 B1 | 11/2010 |
| KR | 101250628 B1 | 4/2013 |
| KR | 20130035392 A | 4/2013 |
| KR | 20140088080 A | 7/2014 |
| WO | 2013060021 A1 | 5/2013 |

OTHER PUBLICATIONS

Jeong, Yeri et al.; "Psychological tactile sensor structure based on piezoelectric nanowire cell arrays;" The Royal Society of Chemistry 2015; RSC Adv., 2015, 5, 40363-40368.

Kuehn, Johannes; "An Artificial Robot Nervous System to Teach Robots How to Feel Pain and Reflexively React to Potentially Damaging Contacts;" IEEE Robotics and Automation Letters, vol. 2, No. 1, Jan. 2017, pp. 72-80. (Published Mar. 1, 2016.).

Long Lin et al., "Triboelectric Active Sensor Array for Self-Powered Static and Dynamic Pressure Detection and Tactile Imaging," ACS Nano, 2013, 7 (9), pp. 8266-8274, Publication Date (Web): Aug. 19, 2013.

* cited by examiner

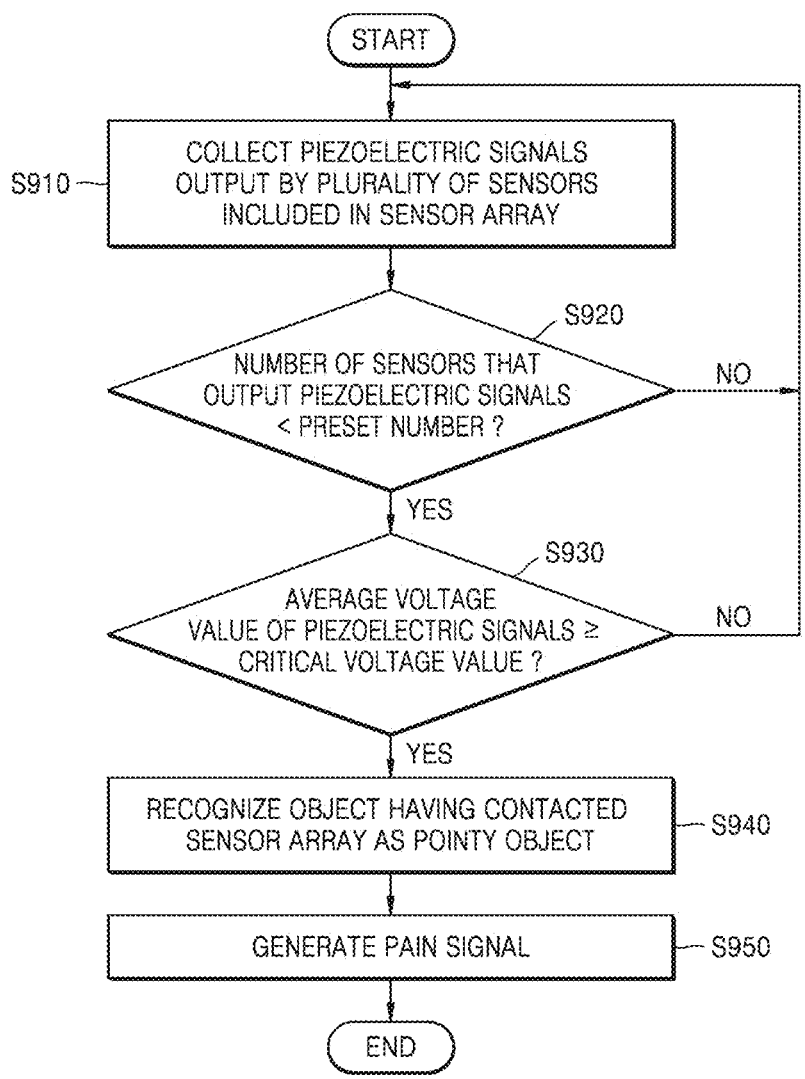

METHOD AND DEVICE FOR SENSING PAIN

CROSS-REFERENCE TO THE RELATED PATENT APPLICATION

This application is a continuation of U.S. Utility patent application Ser. No. 15/235,395, filed on Aug. 12, 2016, which claims priority from Korean Patent Application No. 10-2015-0114711, filed on Aug. 13, 2015, in the Korean Intellectual Property Office, the disclosures of which is are incorporated herein in their entireties by reference.

BACKGROUND

1. Field

One or more embodiments relate to methods and devices for sensing a pain, and more particularly, to a method and device for sensing a pain generated due to a contact of an object by using a piezoelectric material.

2. Description of the Related Art

Recently, artificial tactile sensors have been applied to various applications from simple input systems of mobile devices to complicated finger systems of android robots and have been studied in attempts to mimic the human sense of touch.

For human beings, psychological feeling such as softness, roughness or pain is important for interactions with other humans and objects. Furthermore, pain is an essential feeling that protects the human body from sharp objects such as a knife, a needle, or a nail.

Because a hand of a human can feel pain, when the hand is pricked by a needle or thorn, the human may minimize damage to his or her hand by immediately react to the prick.

However, existing artificial tactile sensors applied to touch panels or robot hands so far simply detect pressure without generation of psychological feelings or focus on achieving a grip control to hold an egg or some other fragile object.

If a pain sensing device, such as an artificial tactile sensor capable of generating an artificial pain signal, is developed, an android robot hand or mobile phone touch display including the pain sensing device can be better protected from contact with sharp objects or from harsh environments. However, devices for generating psychological feeling of a human, such as pain, have not been developed so far.

SUMMARY

One or more embodiments include a pain sensing device capable of sensing psychological feeling of a human, such as pain, and a pain sensing method performed by the pain sensing device.

Additional aspects will be set forth in part in the description which follows and, in part, will be apparent from the description, or may be learned by practice of the presented embodiments.

According to one or more embodiments of the present invention, a pain sensing device includes a sensor array comprising a plurality of sensors that sense pressure generated due to a contact of an object and output electrical piezoelectric signals; and a signal processor configured to recognize the shape of the object based on the number of sensors that output the piezoelectric signals among the plurality of sensors, and to generate a pain signal according to the recognized shape of the object.

According to one or more embodiments of the present invention, a pain sensing method includes sensing pressure generated due to a contact of an object and outputting electrical piezoelectric signals, wherein the sensing of the pressure and the outputting of the electrical piezoelectric signals are performed by a plurality of sensors included in a sensor array; recognizing the shape of the object, based on the number of sensors that output the electrical piezoelectric signals among the plurality of sensors, wherein the recognizing is performed by a signal processor; and generating a pain signal according to the recognized shape of the object, wherein the generating is performed by the signal processor.

BRIEF DESCRIPTION OF THE DRAWINGS

These and/or other aspects will become apparent and more readily appreciated from the following description of the embodiments, taken in conjunction with the accompanying drawings in which:

FIG. 9 is a flowchart of a method of sensing a pain by using the pain sensing device of FIG. 1, according to an embodiment of the present invention.

DETAILED DESCRIPTION

Figure 1:
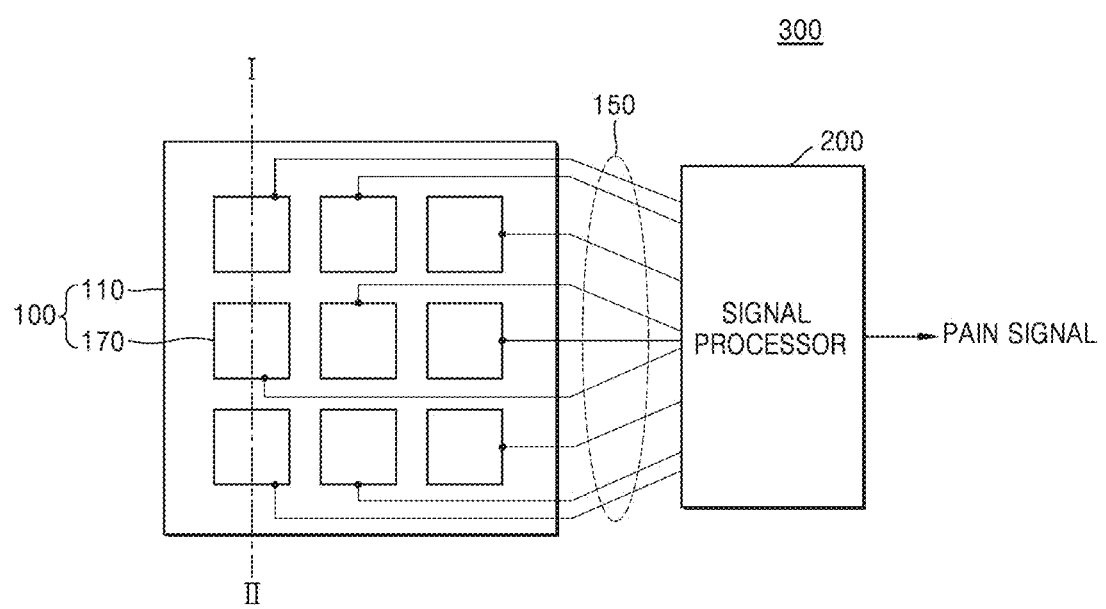
FIG. 1 is a schematic diagram of a structure of a pain sensing device according to an embodiment of the present invention.

Reference will now be made in detail to the exemplary embodiments which are described in reference to the accompanying drawings, wherein like reference numerals refer to like elements throughout. In this regard, the embodiments may have different forms and should not be construed as being limited to the descriptions set forth herein. Accordingly, the embodiments are merely described below, by referring to the figures, to explain aspects of the embodiments. As used herein, the term "and/or" includes any and all combinations of one or more of the associated listed items. Expressions such as "at least one of," when preceding a list of elements, modify the entire list of elements and do not modify the individual elements of the list.

Since the inventive concept may have various modifications and several embodiments, exemplary embodiments are shown in the drawings and will be described in detail. Advantages, features, and a method of achieving the same will be specified with reference to the embodiments described below in detail together with the attached drawings. However, the embodiments may have different forms and should not be construed as being limited to the descriptions set forth herein.

It will be understood that although the terms "first", "second", etc. may be used herein to describe various components, these components should not be limited by these terms. These components are only used to distinguish one component from another.

Singular expressions, unless defined otherwise in contexts, include plural expressions.

In the embodiments below, it will be further understood that the terms "comprise" and/or "have" used herein specify the presence of stated features or components, but do not preclude the presence or addition of one or more other features or components.

In the embodiments below, it will be understood when a portion such as a layer, an area, or an element is referred to as being "on" or "above" another portion, it can be directly on or above the other portion, or intervening portion may also be present.

Also, in the drawings, for convenience of description, sizes of elements may be exaggerated or contracted. In other words, since sizes and thicknesses of components in the drawings are arbitrarily illustrated for convenience of explanation, the following embodiments are not limited thereto.

Figure 2:
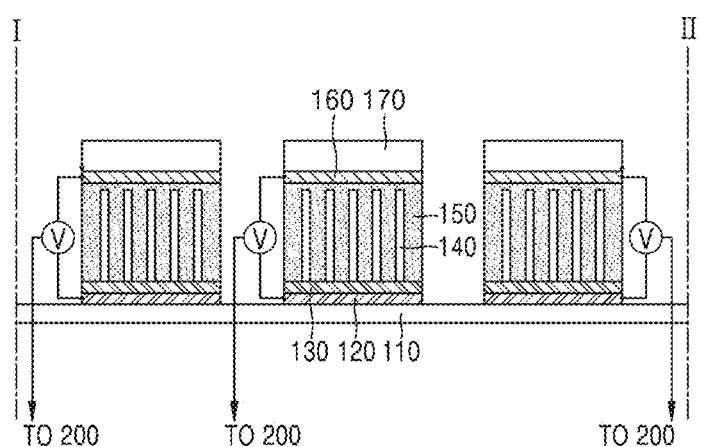
FIG. 2 is a cross-sectional view taken along line II-II' of FIG. 1.

FIG. 1 is a schematic diagram of a structure of a pain sensing device 300 according to an embodiment of the present invention. FIG. 2 is a cross-sectional view taken along line II-II' of FIG. 1.

Referring to FIGS. 1 and 2, the pain sensing device 300 according to an embodiment of the present invention includes a piezoelectric nanowire sensor array 100 that measures a pressure applied thereto by an object, and a signal processor 200 that processes a result of the measurement by the piezoelectric nanowire sensor array 100.

The piezoelectric nanowire sensor array 100 includes a plurality of sensors between a lower substrate 110 and an upper substrate 170.

Each of the plurality of sensors senses a pressure generated by a contact of an object and outputs an electrical piezoelectric signal corresponding to the sensed pressure. The sensors may be piezoelectric nanowire sensors based on a material including a plurality of piezoelectric nanowires. Hereinafter, it is assumed that the sensors are piezoelectric nanowire sensors.

The signal processor 200 is electrically connected to the sensor array 100 by a plurality of wires 150, and receives piezoelectric signals transmitted via the plurality of wires 150.

The signal processor 200 collects the piezoelectric signals output by the plurality of sensors via the plurality of wires 150 and analyzes the collected piezoelectric signals to analyze a distribution pattern of the sensors that output the piezoelectric signals.

The signal processor 200 recognizes the shape of the object that applies a pressure, based on the analyzed distribution pattern of the sensors, and generates a pain signal according to the recognized shape of the object.

The sensor array 100 will now be described in detail.

Referring to FIG. 2, the sensor array 100 includes a lower substrate 110, the upper substrate 170 opposite to the lower substrate 110, and a plurality of piezoelectric nanowire sensors between the lower substrate 110 and the upper substrate 170. According to the present embodiment, for simplification of the drawing, it is assumed that the sensor array 100 includes 9 piezoelectric nanowire sensors. Accordingly, the sensor array 100 may include more piezoelectric nanowire sensors than the 9 piezoelectric nanowire sensors.

In detail, each of the plurality of piezoelectric nanowire sensors includes a lower electrode 120 on the lower substrate 110, a plurality of piezoelectric nanowires 140 vertically grown on the lower electrode 120, a planarization layer 150 that caps the piezoelectric nanowires 140, and an upper electrode 160 on the planarization layer 150. The upper substrate 170 is on the upper electrode 160.

The lower substrate 110 and the upper substrate 170 may be flexible substrates. However, embodiments are not limited thereto, and the lower substrate 110 and the upper substrate 170 may be substrates formed of various other materials. The thicknesses, areas, or shapes of the lower substrate 110 and the upper substrate 170 are not limited.

The lower electrode 120 is on the lower substrate 110 and may be a typical transparent conductive layer. A representative example of the transparent conductive layer may be indium tin oxide (ITO). However, embodiments of the present invention are not limited thereto. The thickness of the lower electrode 120 is not limited and thus may be nanoscale.

The plurality of piezoelectric nanowires 140 are grown vertically on the lower electrode 120, and may include zinc oxide (ZnO), lead-zirconium-titanium oxide (PZT), barium titanate ($BaTiO_3$), tron lithium titanium oxide ($SrTiO_3$), lead titanate ($PbTiO_3$), aluminum nitride (AlN), gallium nitride (GaN), polyvinylidene fluoride (PVDF), or silicon carbide (SiC). To grow the piezoelectric nanowires 140, a seed layer 130 may be formed on the lower electrode 120. The height of the piezoelectric nanowires 140 is not limited, and thus the piezoelectric nanowires 140 may have nanoscale to microscale heights.

The planarization layer 150 caps the plurality of piezoelectric nanowires 140. The piezoelectric nanowires 140 are completely capped by the planarization layer 150, and gaps between the piezoelectric nanowires 140 are filled with the planarization layer 150. The planarization layer 150 may be formed of polysilazane ($SiO_2$), silsesquioxane polymer, and a silane compound to have flexibility.

The upper electrode 160 is on the planarization layer 150, and transmits an electrical piezoelectric signal together with the lower electrode 120. The upper electrode 160 may be a transparent conductive layer, similar to the lower electrode 120.

When a pressure (or a force) is applied to at least one of the lower substrate 110 and the upper substrate 170, the two substrates 110 and 170 are pressed against each other or bent, and thus an electrical piezoelectric signal may be generated from the piezoelectric nanowires 140 disposed between the two substrates 110 and 170.

The signal processor 200 will now be described in detail.

Figure 3:
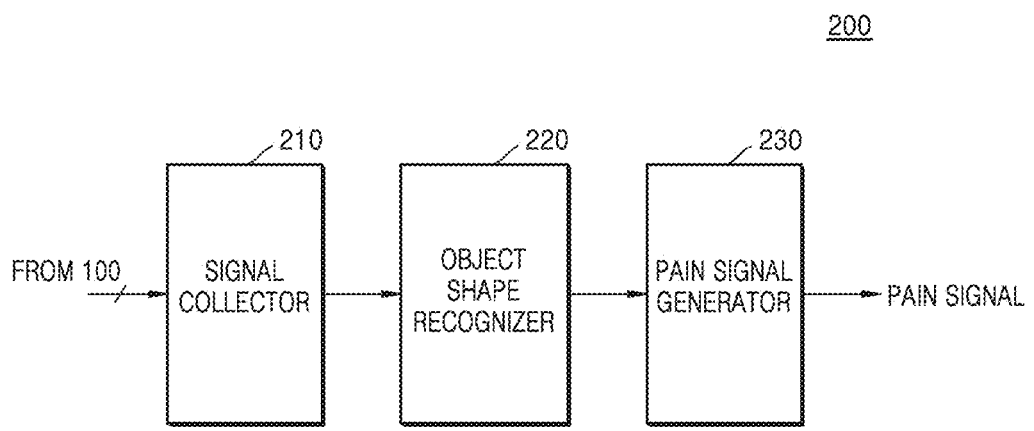
FIG. 3 is a schematic block diagram of a signal processor included in the pain sensing device of FIG. 1.

FIG. 3 is a schematic block diagram of the signal processor 200 of FIG. 1.

Referring to FIG. 3, the signal processor 200 analyzes the piezoelectric signals measured by the plurality of sensors of the sensor array 100, and thus analyzes the distribution pattern of the sensors having sensed the pressure according to a contact of the object. The signal processor 200 recognizes the shape of the object by using a result of the analysis and generates a pain signal according to the recognized shape of the object.

To this end, the signal processor 200 includes a signal collector 210, an object shape recognizer 220, and a pain signal generator 230.

The signal collector 210 collects the piezoelectric signals measured by the plurality of sensors of the sensor arrays 100, and may be implemented using memory. The signal collector 210 provides the collected piezoelectric signals to the object shape recognizer 220 at the request of the object shape recognizer 220.

The object shape recognizer 220 analyzes the piezoelectric signals received from the signal collector 210 to analyze a distribution pattern of the sensors that output the piezoelectric signals, namely, sensors that electrically react to the contact of the object.

Further, the object shape recognizer 220 analyzes the shape of the object having applied the pressure (or force) to the plurality of sensors of the sensor array 100, based on a result of the analysis of the distribution pattern.

The distribution pattern is analyzed based on the number of sensors that output the piezoelectric signals. Via the analysis of the distribution pattern, the shape of the object may be inferred.

Figure 4A:
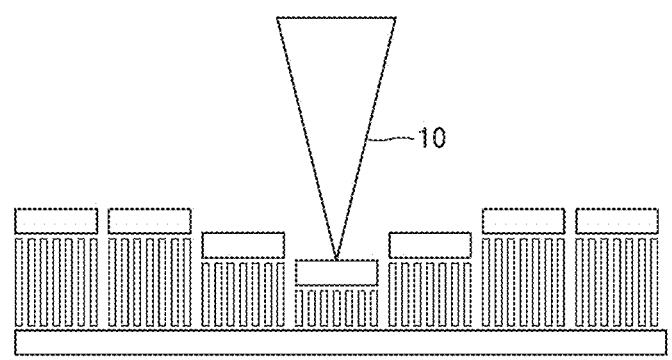
FIGS. 4A and 4B illustrate a distribution pattern of sensors that output piezoelectric signals when a sharp object contacts a sensor array, according to an embodiment of the present invention.
Figure 4B:
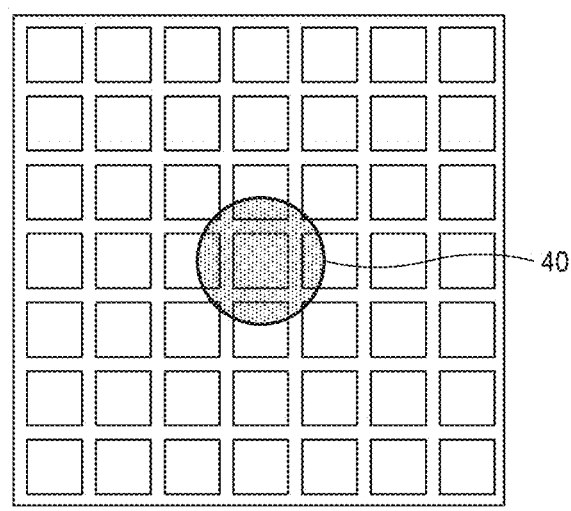
Figure 5A:
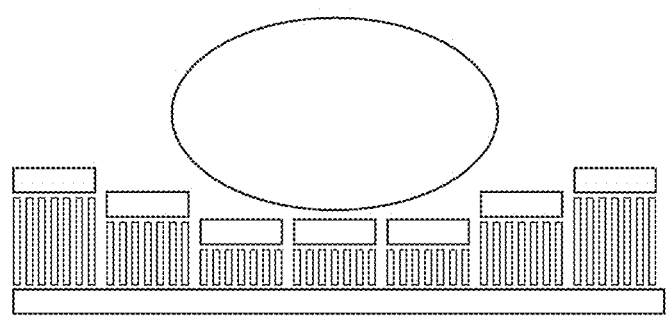
FIGS. 5A and 5B illustrate a distribution pattern of sensors that output piezoelectric signals when a blunt object contacts a sensor array, according to an embodiment of the present invention.
Figure 5B:
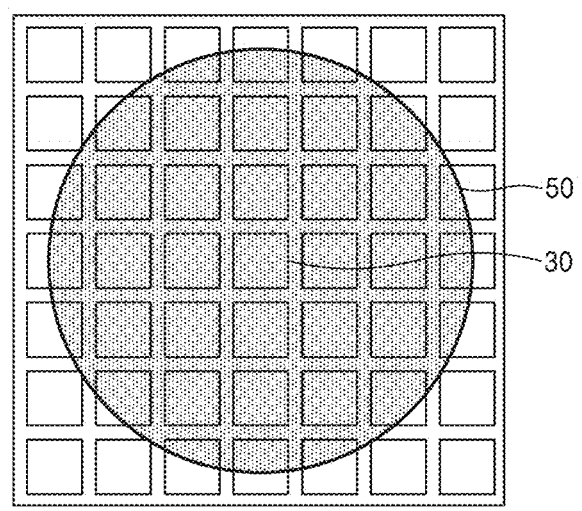

FIGS. 4A and 4B illustrate a distribution pattern of sensors that output piezoelectric signals when a sharp object contacts the sensor array, and FIGS. 5A and 5B illustrate a distribution pattern of sensors that output piezoelectric signals when a blunt object contacts the sensor array, according to an embodiment of the present invention.

As shown in FIG. 4A, when an object 10 having a pointy or sharp shape contacts the sensor arrays 100, a pressure (or force) applied by the object 10 may be sensed by only one sensor or a few sensors of the sensor arrays 100. Accordingly, the sensors that electrically react to the contact of the object 10 form a distribution pattern 40 having a narrow range, as shown in FIG. 4B.

On the other hand, as shown in FIG. 5A, when an object 20 having a blunt shape contacts the sensor arrays 100, a pressure (or force) applied by the object 20 may be sensed by a plurality of sensors of the sensor arrays 100. Accordingly, the sensors that electrically react to the contact of the object 20 form a distribution pattern 50 having a wide range and including a center sensor 30 and a plurality of sensors adjacent to the center sensor 30, as shown in FIG. 5B.

Thus, when the number of sensors that output the piezoelectric signals is less than a preset number, the object shape recognizer 220 recognizes the object currently in contact with the sensor array 100 as a pointy or sharp object. On the other hand, when the number of sensors that output the piezoelectric signals exceeds the preset number, the object shape recognizer 220 recognizes the object currently in contact with the sensor array 100 as a blunt object. Because the number of sensors that react to a contact of a pointy or sharp object increases as the total number of sensors increases, the preset number may be appropriately set by taking into account the overall number of sensors included in the sensor array 100.

As such, when the object shape recognizer 220 recognizes the shape of the object, the object shape recognizer 220 transmits a result of the recognition to the pain signal generator 230, and the pain signal generator 230 generates a pain signal based on the result of the recognition.

In other words, in response to a recognition result indicating that an object currently in contact with the sensor array 100 is a pointy or sharp object, the pain signal generator 230 performs an operation of generating a pain signal. In response to a recognition result indicating that an object currently in contact with the sensor array 100 is a blunt object, the pain signal generator 230 does not perform the operation of generating a pain signal.

Each sensor of the sensor array 100 may output a piezoelectric signal of a fine magnitude due to a leakage current even when there are no contacts of an object. The piezoelectric signal of the fine magnitude needs to be ignored. Therefore, only a piezoelectric signal having a voltage equal to or greater than a critical voltage value corresponding to pain needs to be used as a reference signal for generating a pain signal.

Accordingly, even when the pain signal generator 230 receives from the object shape recognizer 220 a recognition result indicating that an object currently in contact with the sensor array 100 is a pointy or sharp object, if the voltage value of a piezoelectric signal used in the recognition result is less than the critical voltage value, the pain signal generator 230 does not perform the operation of generating a pain signal.

As such, the pain signal generated by the pain signal generator 230 may be utilized in various systems for preventing physical damages of specific electronic apparatuses, such as a hand system of an android robot and a display panel of a mobile phone.

Although the signal processor 200 includes three components, namely, the signal collector 210, the object shape recognizer 220, and the pain signal generator 230, in FIG. 3, this is only a division according to functions in order to facilitate understanding of explanation, and thus embodiments are not limited thereto. Accordingly, it is obvious to one of ordinary skill in the art that these components may be implemented using a single chip including a memory, a central operation processor, and a comparator.

Figure 6A:
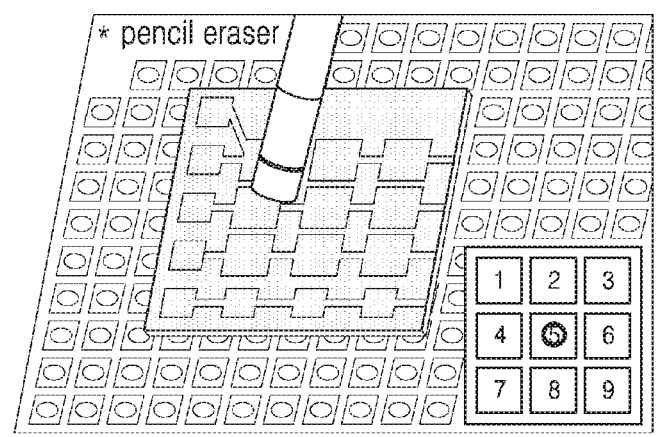
FIGS. 6A, 6B, and 6C show results of signals detected by each sensor of a sensor array when a blunt object contacts the sensor array, according to an embodiment of the present invention.
Figure 6A:
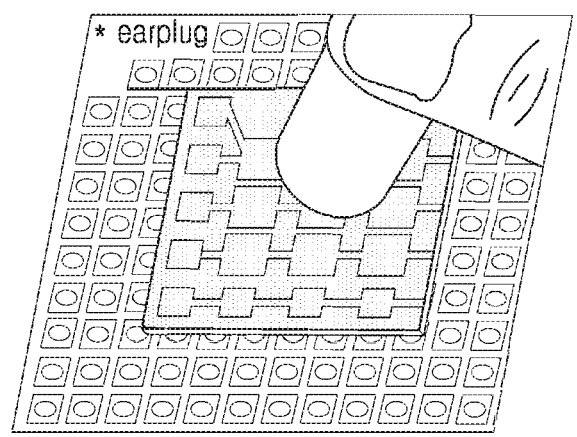
Figure 6B:
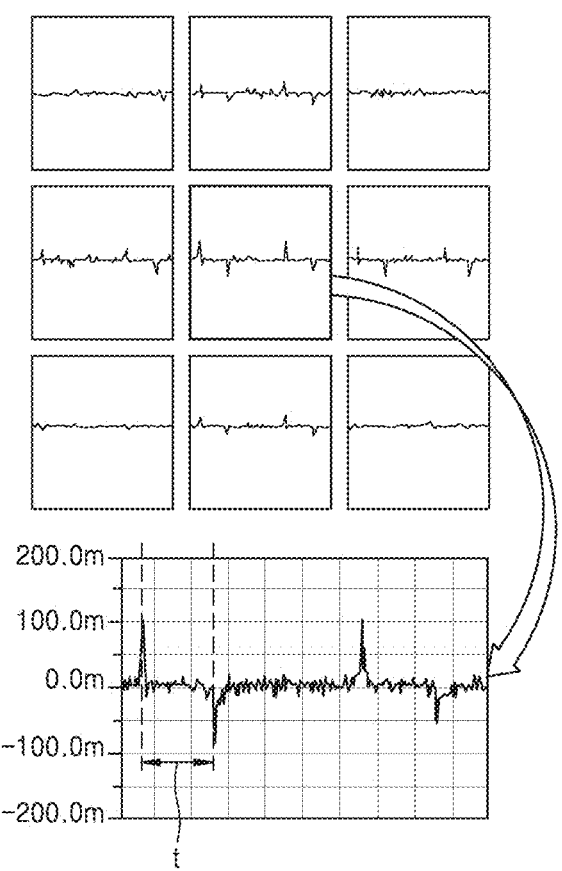
Figure 6C:
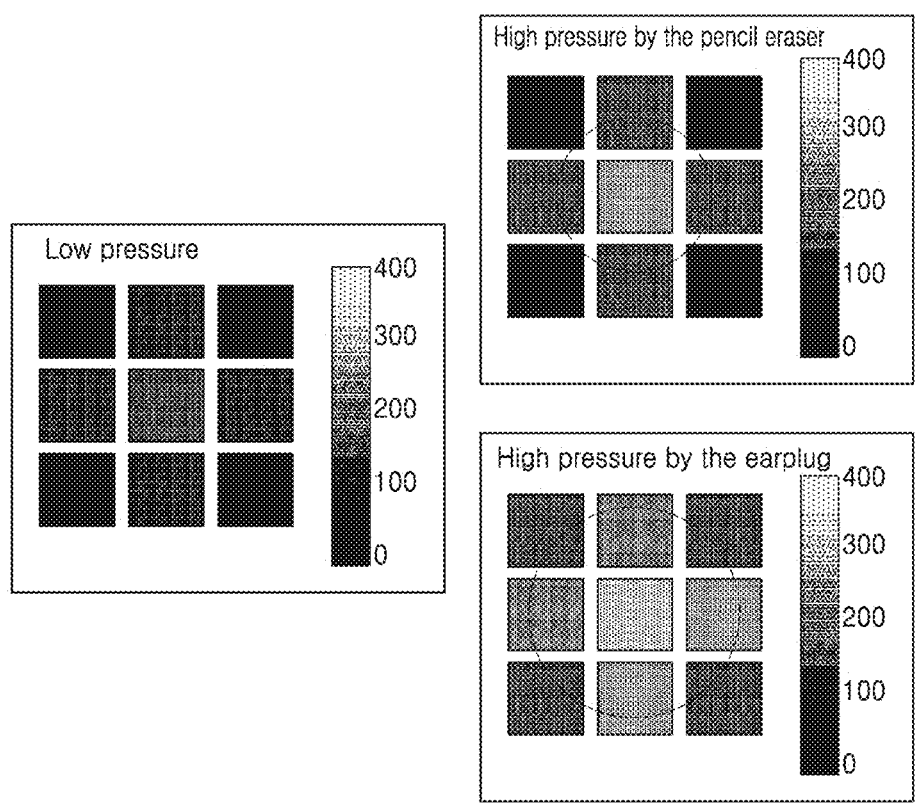

FIGS. 6A, 6B, and 6C show results of signals detected by each sensor of a sensor array when a blunt object contacts the sensor array, according to an embodiment of the present invention.

FIG. 6A show photo images of two blunt objects on a center sensor of a sensor array according to an embodiment of the present invention. An upper photo image is a photo image of a pencil eraser, and a lower photo image is a photo image of an earplug that is in contact with the center sensor of the sensor array.

As shown in FIG. 6B, electrical piezoelectric signals are detected due to deformation of the piezoelectric nanowires of all of the sensors of the sensor array. In FIG. 6C, respective pressures sensed by the sensors are expressed in different degrees of shade.

When the pencil eraser or the earplug contacts the sensor array at a low pressure, contact points are generated on a center region of the sensor array such that the center sensor may generate a piezoelectric signal of 100 mV and sensors adjacent to the center sensor may generate piezoelectric signals of no more than 50 mV. On the contrary, any signals are not detected from sensors located at four corners and not in contact with the pencil eraser or the earplug. A left view in FIG. 6C, the sensors located at four corners and not in contact with the pencil eraser or the earplug were displayed in a black color.

A lower voltage graph of FIG. 6B is a magnification of a voltage graph of a piezoelectric signal detected by a center sensor 5 among upper voltage graphs of FIG. 6B. In the magnified voltage graph, 't' represents the length of a pressure maintenance duration of the pencil eraser.

A right upper view in FIG. 6C represents a voltage level in each of the plurality sensors when the pencil eraser pressed the sensor array with high pressure. In the center sensor, a piezoelectric signal at a highest pressure has a voltage of about 250 mV.

When 200 mV is set to be a critical voltage value corresponding to pain, the piezoelectric signal of about 250 mV may be used as a signal that may be recognized as pain. However, according to the present invention, a pain signal is not generated based on only the voltage value of a piezoelectric signal but also the number of sensors that output piezoelectric signals and a distribution of the sensors are considered as estimation factors for generating a pain signal. Thus, even if the piezoelectric signal has about 250 mV, the pain signal may not be generated.

A right lower view in FIG. 6C represents a voltage level in each of the plurality sensors when the earplug pressed the sensor array with high pressure. In the center sensor, a piezoelectric signal at a highest pressure has a voltage of about 300 mV. Because the earplug is larger than the pencil eraser, a contact of the earplug is detected from a larger area of the sensor array than an area from which a contact of the pencil eraser is detected, at the same pressure as the pressure applied by the pencil eraser. However, no pain signals are generated when considering the number of sensors that output piezoelectric signals and a distribution of the sensors.

Figure 7A:
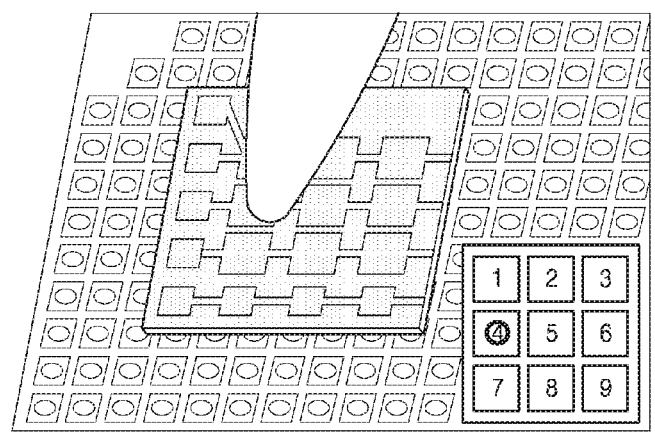
FIGS. 7A, 7B, and 7C show a result of a signal detected by each sensor of a sensor array when a sharp object contacts the sensor array, according to an embodiment of the present invention.
Figure 7A:
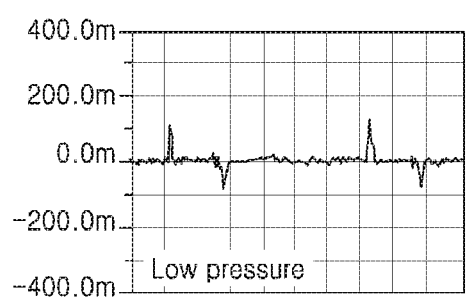
Figure 7A:
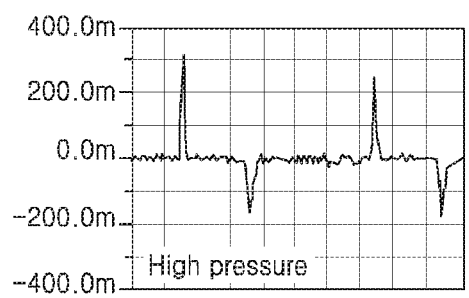
Figure 7B:
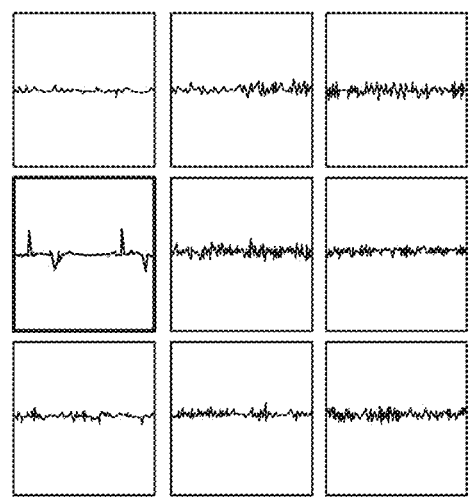
Figure 7B:
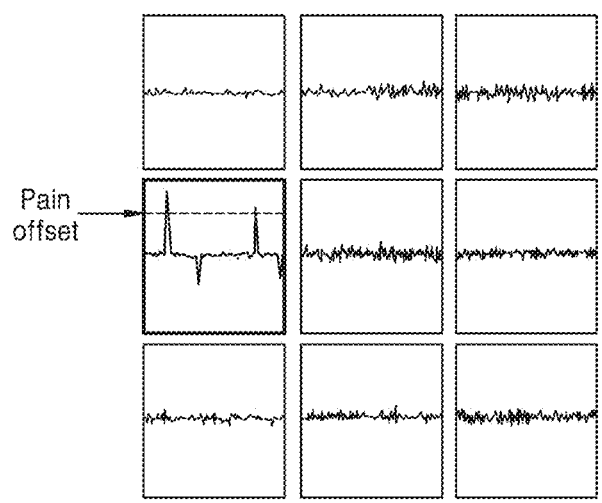
Figure 7C:
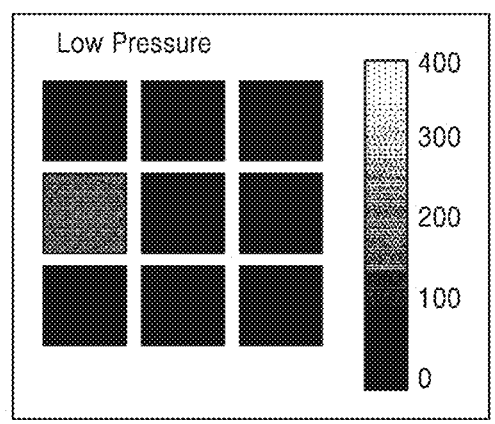
Figure 7C:
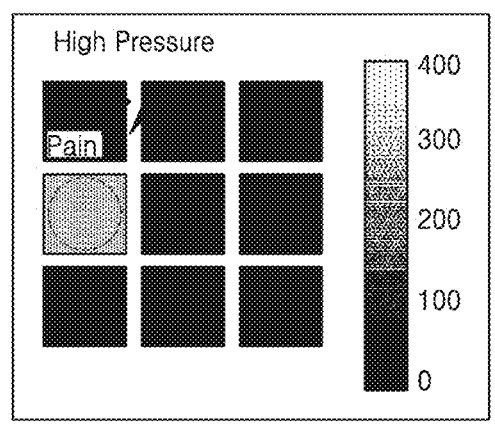

FIGS. 7A, 7B, and 7C show a result of a signal detected by each sensors of a sensor array when a sharp object contacts the sensor array, according to an embodiment of the present invention.

FIG. 7A shows a photo image of a sharp pen cap that is in contact with a sensor 4 of a sensor array according to an embodiment of the present invention, a voltage graph of a piezoelectric signal detected by the sensor 4 when the pen cap contacts the sensor 4 at a low pressure, and a voltage graph of a piezoelectric signal detected by the sensor 4 when the pen cap contacts the sensor 4 at a high pressure.

Because the pen cap applies a pressure to only the sensor 4 due to the sharp shape of the pen cap, sensors adjacent to the sensor 4 do not generate piezoelectric signals.

As can be seen from an upper graph of FIG. 7A, because the sensor 4 generates a piezoelectric signal of 100 mV that is lower than a preset critical voltage value (i.e., a pain offset) of 200 mV at a low pressure, no pain signals are generated.

On the other hand, as can be seen from a lower graph of FIG. 7A, because the sensor 4 generates a piezoelectric signal of 300 mV that is higher than the preset critical voltage value of 200 mV at a high pressure, a pain signal is generated.

An upper portion of FIG. 7B shows voltage graphs of piezoelectric signals respectively detected by 9 sensors of a sensor array when the pen cap contacts the sensor array at a low pressure, and a lower portion of FIG. 7B shows voltage graphs of piezoelectric signals respectively detected by the 9 sensors when the pen cap contacts the sensor array at a high pressure. In FIG. 7C, the sensor 4 that applies a low pressure is displayed in dark gray, and the sensor 4 that applies a high pressure is displayed in bright gray.

Figure 8:
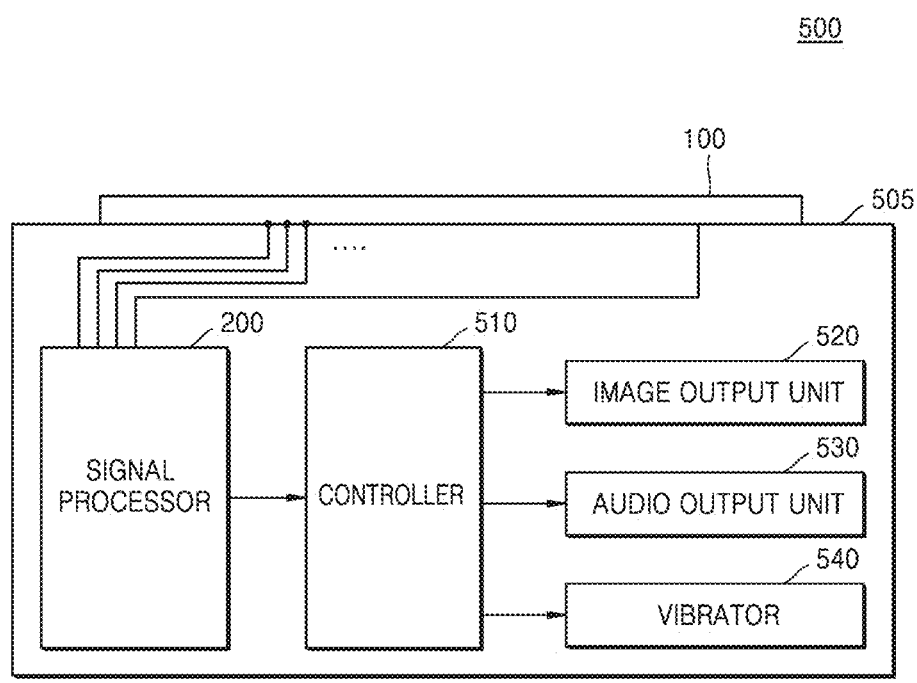
FIG. 8 is a block diagram of a structure of an electronic apparatus to which a pain sensing device according to an embodiment of the present invention is applied.

FIG. 8 is a block diagram of a structure of an electronic apparatus 500 to which a pain sensing device according to an embodiment of the present invention is applied.

Referring to FIG. 8, the electronic apparatus 500 to which the pain sensing device according to an embodiment of the present invention is applied may be a hand system of a robot or a mobile phone. However, the pain sensing device according to an embodiment of the present invention is applied to not only a mobile phone or a hand system of a robot, but may also be applied to all kinds of electronic apparatuses that need to be protected from a contact of an external object.

In detail, the electronic apparatus 500 includes the sensor array 100, the signal processor 200, a controller 510, an image output unit 520, an audio output unit 530, and a vibrator 540.

The structures and functions of the sensor array 100 and the signal processor 200 have been fully described above with reference to FIGS. 1-7, and thus repeated descriptions thereof will be omitted. However, the sensor array 100 may be provided in a housing of the electronic apparatus 500. Alternatively, when the electronic apparatus 500 includes a display panel, the sensor array 100 may be provided on the display panel.

The controller 510 controls overall operations of the components included in the electronic apparatus 500.

When a pointy or sharp object contacts the sensor array 100 at a certain pressure or higher, the controller 510 receives an electrical pain signal corresponding to the pressure from the signal processor 200 and generates a plurality of pain control signals for controlling the image output unit 520, the audio output unit 530, and the vibrator 540 according to the electrical pain signal.

Although not shown in FIG. 8, the image output unit 520 may include a driver and a display panel that are used to output an image.

The driver of the image output unit 520 outputs a driving signal according to a pain control signal generated by the controller 510.

The display panel of the image output unit 520 may output various pieces of visual information that represent the pain control signal, in response to the driving signal. The visual information may be information in the form of a texture, a graphic, or a combination thereof. A user is able to check display information displayed on the display panel, recognize that a pointy object is applying a physical pressure to the electronic apparatus 500, and take an immediate subsequent measure, such as separating the pointy object from the electronic apparatus 500.

The audio output unit 530 may output an audio signal according to a pain control signal generated by the controller 510. The audio output unit 530 may be implemented using an amplifier, a speaker, a filter, or the like. The user is able to acoustically check the audio signal output via the audio output unit 530, recognize that a pointy object is applying a physical pressure to the electronic apparatus 500, and take an immediate subsequent measure.

The vibrator 540 may generate a vibration according to a pain control signal generated by the controller 510. To generate the vibration, although not shown in FIG. 8, the vibrator 540 may include a motor driver and a vibration motor. The user is able to tactually check the vibration generated by the vibrator 540, recognize that a pointy object is applying a physical pressure to the electronic apparatus 500, and take an immediate subsequent measure.

FIG. 9 is a flowchart of a method of sensing a pain by using the pain sensing device 300, according to an embodiment of the present invention. To help understanding of an explanation, FIG. 1 is also referred to.

Referring to FIGS. 1 and 9, first, when an object having a specific shape contacts the sensor array 100, the signal processor 200 collects piezoelectric signals output by a plurality of sensors included in the sensor array 100, in operation S910. Each sensor of the sensor array 100 may be a piezoelectric nanowire sensor based on piezoelectric nanowires.

Then, the signal processor 200 analyzes a distribution pattern of the sensors that output the piezoelectric signals, in operations S920 and S930.

In detail, in operation S920, the signal processor 200 compares the number of sensors that output the piezoelectric signals with a preset number. When the number of sensors that output the piezoelectric signals is less than the preset number, the method proceeds to operation S930.

Otherwise, the method is fed back to an operation prior to operation S910, and a standby state is maintained until a next piezoelectric signal is collected.

Then, in operation S930, an average voltage value of the piezoelectric signals is compared with a critical voltage value. The critical voltage value is a preset reference voltage value for determining pain.

Then, if the average voltage value of the piezoelectric signals collected by sensors the number of which is less than the preset number is equal to or greater than the critical voltage value in operation S930, the object having contacted the sensor array 100 is recognized as a pointy object, in operation S940. On the other hand, if the average voltage value of the piezoelectric signals collected by sensors the number of which is less than the preset number is less than the critical voltage value in operation S930, the method is fed back to an operation prior to operation S910, and a standby state is maintained until a next piezoelectric signal is collected.

Then, in operation S950, when the object having contacted the sensor array 100 is recognized as a pointy object, the signal processor 200 generates a pain signal. The generated pain signal may be used in a system for protecting various electronic apparatuses, such as a mobile phone and a hand system of an android robot, from an external pressure of an object.

As described above, according to the present invention, each sensor of a sensor array capable of measuring a pressure based on a piezoelectric nanowire material independently measures a pressure applied by an object.

As described above, when a blunt object, such as a pencil eraser, contacts a sensor array, a plurality of sensors generate similar piezoelectric signals. Thus, when a distribution pattern is analyzed from the piezoelectric signals, the shape of the object that is in contact with the sensor array may be inferred. When the shape of the blunt object is inferred, no pain signals are generated.

On the other hand, when a pointy object, such as a pencil lead or a needle, contacts a sensor array, a pressure is measured by only one or a few sensors. Thus, a pressure distribution pattern of the sensors that react to the pressure is analyzed based on the measurement of pressure by only one or a few sensors, and thus a pointy object such as a needle may be inferred. When the pointy object is inferred in this way and a voltage value of the piezoelectric signals output by the sensors is equal to or greater than a critical voltage value, a pain signal is generated.

According to the present invention, the shape of an object may be recognized via a distribution pattern of the sensors that react to a contact of the object, and an artificial pain signal may be generated according to the recognized shape of the object.

Accordingly, an electronic apparatus, such as a robot hand to which the present invention is applied or a touch display of a mobile phone to which the present invention is applied may be prevented from being damaged by a contact of a sharp object or by harsh environments, and thus may stably operate.

The exemplary embodiments should be considered in descriptive sense only and not for purposes of limitation. Descriptions of features or aspects within each embodiment should typically be considered as available for other similar features or aspects in other embodiments.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A pain sensing device comprising:
a sensor array comprising a plurality of sensors that sense pressure generated due to a contact of an object and output electrical piezoelectric signals; and
a signal processor configured to generate a pain signal based on a comparison of a number of sensors that are disposed adjacent to a center sensor and output the piezoelectric signals among the plurality of sensors with a predetermined number,
wherein the center sensor is the sensor with the highest voltage value of the piezoelectric signals among the plurality of sensors,
wherein the signal processor generates the pain signal, when the number of sensors that are disposed adjacent to the center sensor and output the electrical piezoelectric signals is less than a preset number, and a voltage value of the piezoelectric signals is equal to or greater than a critical voltage, and
wherein the signal processor generates the pain signal depending on a distribution pattern of the sensors that output the piezoelectric signal, wherein the distribution pattern is set by a difference between the voltage value of piezoelectric signal of the center sensor and the voltage values of the piezoelectric signals of the sensors that disposed adjacent to the center sensor and the total number of sensors included in the sensor array.

2. The pain sensing device of claim 1, wherein the signal processor does not generate a pain signal when the number of sensors that output the electrical piezoelectric signals exceeds a preset number.

3. The pain sensing device of claim 1, wherein each of the plurality of sensors is a piezoelectric nanowire sensor based on piezoelectric nanowires.

4. The pain sensing device of claim 3, wherein the piezoelectric nanowires comprise zinc oxide (ZnO), lead-zirconium-titanium oxide (PZT), barium titanate ($BaTiO_3$), tron lithium titanium oxide ($SrTiO_3$), lead titanate ($PbTiO_3$), aluminum nitride (AlN), gallium nitride (GaN), polyvinylidene fluoride (PVDF), or silicon carbide (SiC).

5. A pain sensing method comprising:
sensing a contact of an object and outputting electrical signals by a plurality of sensors included in a sensor array;
comparing a number of sensors that are disposed adjacent to a center sensor and output the electrical signals among the plurality of sensors with a predetermined number by a signal processor; and
generating a pain signal according to a comparison result by the signal processor,
wherein the center sensor is the sensor with the highest voltage value of the piezoelectric signals among the plurality of sensors,
wherein the signal processor generates the pain signal, when the number of sensors that are disposed adjacent to the center sensor and output the electrical piezoelectric signals is less than a preset number, and a voltage value of the piezoelectric signals is equal to or greater than a critical voltage, and wherein the signal processor generates the pain signal depending on a distribution pattern of the sensors that output the piezoelectric signal, wherein the distribution pattern is set by a difference between the voltage value of piezoelectric signal of the center sensor and the voltage values of the piezoelectric signals of the sensors that disposed adjacent to the center sensor and the total number of sensors included in the sensor array.

6. The pain sensing method of claim 5, further comprising:

generating pain control signals for controlling at least one of an image output unit, an audio output unit, and a vibrator corresponding to the pain signal by a controller, outputting at least one of a visual information, an audio signal, a vibration by the at least one of the image output unit, the audio output unit and the vibrator.

7. A pain sensing device comprising:

a sensor array comprising a plurality of sensors that sense a contact of an object and output electrical signals; and a signal processor configured to generate a pain signal based on a comparison of a number of sensors that are disposed adjacent to a center sensor and output the signals among the plurality of sensors with a predetermined number, wherein the center sensor is the sensor with the highest voltage value of the piezoelectric signals among the plurality of sensors, wherein the signal processor generates the pain signal, when the number of sensors that are disposed adjacent to the center sensor and output the electrical piezoelectric signals is less than a preset number, and a voltage value of the piezoelectric signals is equal to or greater than a critical voltage, and wherein the signal processor generates the pain signal depending on a distribution pattern of the sensors that output the piezoelectric signal, wherein the distribution pattern is set by a difference between the voltage value of piezoelectric signal of the center sensor and the voltage values of the piezoelectric signals of the sensors that disposed adjacent to the center sensor and the total number of sensors included in the sensor array.

\* \* \* \* \*